US006252071B1

(12) United States Patent
Müller et al.

(10) Patent No.: US 6,252,071 B1
(45) Date of Patent: Jun. 26, 2001

(54) AMINOMETHYLATION OF TOCOPHEROLS

(75) Inventors: Robert Karl Müller, Basel; Heinz Schneider, Oberwil, both of (CH)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/532,523

(22) Filed: Mar. 21, 2000

Related U.S. Application Data

(62) Division of application No. 08/620,966, filed on Mar. 22, 1996, now Pat. No. 6,066,731.

(30) Foreign Application Priority Data

Mar. 28, 1995 (CH) ...................................... 878/95

(51) Int. Cl.[7] ...................... C07C 211/09; C07D 207/04; C07D 295/023; C07D 295/04; C07D 413/06
(52) U.S. Cl. .......................... 544/111; 544/357; 544/399; 546/190; 548/524; 564/452; 564/473
(58) Field of Search ................................... 544/111, 357, 544/399; 546/190; 548/524; 564/452, 473

(56) References Cited

U.S. PATENT DOCUMENTS

| | | |
|---|---|---|
| 2,486,539 | 11/1949 | Weisler . |
| 2,519,863 | 8/1950 | Weisler . |
| 4,977,282 | 12/1990 | Baldwin et al. . |
| 5,229,521 | 7/1993 | Luisoli et al. . |

FOREIGN PATENT DOCUMENTS

| | | |
|---|---|---|
| 26667/8 | 6/1989 | (AU) . |
| 0 159 018 | 10/1985 | (EP) . |
| 0 319 834 A2 | 11/1988 | (EP) . |
| 0 490 815 A1 | 12/1991 | (EP) . |

OTHER PUBLICATIONS

Nakamura, et al., "Studies on Tocopherol Derivatives I Conversion of β, γ–, and δ–Tochopherol to α–Tocopherol," *Chem. Pharm. Bull.*, vol. 19 (11), pp. 2318–2324 (1971).

Blicke, "The Mannich Reaction," *Organic Reactions*, vol. 1, Chapter 10, pp. 327–328, 1942.

*Primary Examiner*—Joseph K. McKane
*Assistant Examiner*—Taofiq A. Solola
(74) *Attorney, Agent, or Firm*—Mark E. Waddell; Stephen M. Haracz; Bryan Cave LLP

(57) ABSTRACT

A process for the production of a Mannich reagent comprises reacting formaldehyde, especially paraformaldehyde, with a secondary amine in the complete or almost complete absence of a solvent. An alternative comprises reacting a diaminomethane produced from a secondary amine, formaldehyde, especially paraformaldehyde, as well as water with one another in about equimolar amounts. The invention is also concerned with a process for the aminomethylation of δ-tocopherol or of tocopherol mixtures containing this and comprises using a Mannich reagent which has been produced in the above manner. After completion of this aminomethylation process excess Mannich reagent can be separated by distillation and can be reacted with water and formaldehyde, especially paraformaldehyde, in order to regenerate further Mannich reagent suitable for use in the aminomethylation, this regeneration representing a further aspect of the invention. Finally, the invention includes certain novel bis(aminomethyl)-γ-tocopherols.

15 Claims, No Drawings

AMINOMETHYLATION OF TOCOPHEROLS

This is a divisional of U.S. application Ser. No. 08/620,966, filed Mar. 22, 1996, now U.S. Pat. No. 6,066,731.

BACKGROUND OF THE INVENTION

The present invention is concerned with the aminomethylation of the unsubstituted positions on the benzene ring of tocopherols, especially the complete aminomethylation of δ-tocopherol either alone or as a component of a mixture of several so-called "non-α-tocopherols" containing this tocopherol as well as, e.g., β- and γ-tocopherol.

It is known from the relevant literature that the conversion of δ-tocopherol, which differs from α-tocopherol by the presence of two unsubstituted positions (5- and 7-) on the benzene ring, into the corresponding 5,7-bis(aminomethyl) derivatives takes place only incompletely. An incomplete aminomethylation of δ-tocopherol leads, after the catalytic reduction performed subsequently in order to convert the aminomethylated product to α-tocopherol, to an α/β-tocopherol mixture which can only then be converted into α-tocopherol by an additional reaction cycle of aminomethylation+catalytic reduction. As an alternative to this additional cycle, the initially-produced α-tocopherol can be separated from the mixture of α/β-tocopherols, which of course likewise leads to an unsatisfactorily low yield of α-tocopherol, which tocopherol is preferred for known biological reasons over the non-α-tocopherols. For these reasons, the previously known processes for the aminomethylation of δ-tocopherol have been found to be expensive and accordingly uneconomical, which also applies to the aminomethylation of tocopherol mixtures containing δ-tocopherol.

Thus, Nakamura and Kijima [Chem. Pharm. Bull. 19(11), 2318–2324 (1971)] have reacted δ-tocopherol with in each case eight mol equivalents of aqueous dimethylamine solution and 37% formalin at reflux temperature for 4 hours and in this way obtained (see pages 2320 and 2322) a mixture of the 5-mono-substituted product, 5-dimethylaminomethyl-δ-tocopherol (57% yield), and the 5,7-disubstituted product, 5,7-bis(dimethylamino-methyl)-δ-tocopherol (only 31% yield). This result is obviously due to the fact that the 5-position of the δ-tocopherol molecule is substantially more reactive to aminomethylation than the 7-position and that the substitutability of the still free 7-position is further impeded by the introduction of the first amino substituent. The problem of incomplete aminomethylation is also evident in European Patent Publication (EP) 159 018 of the Henkel Corp., where the aminomethylation of a tocopherol mixture and the subsequent separation of the aminomethylated β-, δ- and γ-tocopherols from the unreacted α-tocopherol are disclosed. After catalytic hydrogenation of the aminomethylated tocopherols, the thus-obtained mixture of α-, β, δ- and γ-tocopherols is again aminomethylated and hydrogenated in order to obtain (see pages 16–19) a product having a high as possible content of α-tocopherol. This second round of aminomethylation and hydrogenation comprises the aforementioned "additional reaction cycle" which the incomplete aminomethylation of the prior art required.

SUMMARY OF THE INVENTION

The object of the present invention is to carry out the aminomethylation of δ-tocopherol or of tocopherol mixtures containing δ-tocopherol as completely and accordingly as economically as possible. This object is achieved by performing the aminomethylation reaction using a Mannich reagent (reaction product of formaldehyde or a formaldehyde-producing compound and a secondary amine) which has been produced by reacting formaldehyde or a formaldehyde-producing compound, preferably paraformaldehyde as the formaldehyde-producing compound, with a secondary amine in the complete or almost complete absence of a solvent. Accordingly, the present invention is concerned with the aminomethylation process carried out in this manner, the process for the production of the Mannich reagent itself, as well as the Mannich reagent produced in this manner.

DETAILED DESCRIPTION OF THE INVENTION

The process in accordance with the invention for the aminomethylation of the unsubstituted positions of the benzene ring of δ-tocopherol or of tocopherol mixtures containing δ-tocopherol comprises reacting the δ-tocopherol or tocopherol mixture with a Mannich reagent which has been produced by reacting formaldehyde or a formaldehyde-producing compound with a secondary amine in the complete or almost complete absence of a solvent. The separate (carried out prior to the actual aminomethylation) production of the Mannich reagent, as well as the thus-produced Mannich reagent itself are further aspects of the present invention.

A Mannich reagent is the product of a reaction between formaldehyde and a secondary amine. The reaction ultimately forms an iminium ion which is the reactive species. However, the iminium ion exists in equilibrium with the reactants and an intermediate hydroxymethyl-secondary amine, as follows:

In accordance with the invention, formaldehyde or a formaldehyde-producing compound may be reacted with the secondary amine to produce the Mannich reagent. For the purposes of this invention, a formaldehyde-producing compound is any compound which acts as a source of formaldehyde to react with the secondary amine to form the Mannich reagent. The preferred formaldehyde-producing compound is paraformaldehyde. For simplicity, reference to formaldehyde herein also includes formaldehyde-producing compounds.

For the production of the Mannich reagent, the formaldehyde is added to the secondary amine portionwise and sufficiently slowly such that the temperature of the reaction mixture does not rise too rapidly (the reaction is exothermic). Moreover, the mixture is preferably stirred during and after completion of the addition. Preferably, between 0.7 and 1.2 mole equivalents of formaldehyde, more preferably between 0.9 and 1.1 mole equivalents, are used per mole equivalent of the secondary amine.

The temperature at which the Mannich reagent is prepared is not critical. Any temperature at which formaldehyde will react with a given secondary amine may be used in accordance with the invention. Since—as mentioned above—the reaction is exothermic, it is usually not necessary to heat the reaction mixture above the required initial reaction temperature which, depending on the secondary amine used, normally lies in the range of about 50° C. to about 70° C. Having regard to the exothermic nature of the reaction, the temperature tends to increase in the course of the reaction by a few degrees, normally by up to about 20 degrees Celsius, i.e. up to about 70° C.–90° C.

Therefore, one aspect of the invention comprises a process for the production of a Mannich reagent, which process comprises reacting formaldehyde in the absence of an inert solvent with a secondary amine of the formula:

wherein $R^1$ and $R^2$ are the same or different and are $C_{1-6}$-alkyl, $C_{2-6}$-hydroxyalkyl or $C_{2-6}$-alkoxyalkyl, or taken together with the nitrogen atom to which they are attached form a 5- to 8-membered heterocyclic ring, which is unsubstituted or substituted by $C_{1-6}$-alkyl, and which heterocyclic ring contains at most one additional heteroatom selected from the group consisting of oxygen and nitrogen,
wherein the ratio of said formaldehyde to said secondary amine in said reaction in mole equivalents is in the range from 0.7:1 to 1.2:1, so that said formaldehyde and said secondary amine are eacted to produce said Mannich reagent.

Preferably, 0.9 to 1.1 mol equivalents of formaldehyde are reacted with 1 mol equivalent of secondary amine. As noted above, the form of formaldehyde used is preferably paraformaldehyde.

In principle, any secondary amine which conventionally comes into consideration for aminomethylation can be used for the production of the Mannich reagent. For practical reasons, there is, however, preferably used a di($C_{1-6}$-alkyl) amine, a di($C_{2-6}$-hydroxyalkyl)amine, a di($C_{2-6}$-alkoxyalkyl)amine or a cyclic amine formed when $R^1$ and $R^2$, above, are taken together with the nitrogen atom to which they are attached. The cyclic amine is a 5- to 8-membered ring compound which contains at most one further heteroatom, either oxygen or nitrogen. The ring can be substituted on the its carbon atoms as well as on the further nitrogen atom optionally present. In the case of a substituted cyclic amine the preferred substitutents are lower alkyl groups ($C_{1-6}$-alkyl groups).

When not taken together with the nitrogen to which they are attached to form a heterocyclic ring, $R^1$ and $R^2$ are preferably independently methyl, ethyl, hydroxyethyl or methoxyethyl. More preferably $R^1$ and $R^2$ are the same. Therefore, examples of dialkylamines are dimethylamine and diethylamine; an example of a di(hydroxyalkyl)amine is di(hydroxyethyl)amine; and an example of a di(alkoxyalkyl) amine is di(methoxyethyl)amine.

When taken together with the nitrogen atom to which they are attached to form a heterocyclic ring, rings of 5 or 6 members are preferred. Examples of such cyclic amines are, pyrrolidine, piperidine, 1-methyl-piperazine and morpholine, of which 1-methyl-piperazine and morpholine are preferred.

The course of the reaction between the formaldehyde and the secondary amine can be followed in a conventional manner. e.g., by NMR analysis of a sample of the reaction mixture. Thereby, it is established that this mixture during the reaction has an ever-increasing content of the respective diaminomethane, e.g., dimorpholinomethane when formaldehyde is reacted with morpholine as the secondary amine. Of course, other components are always present, inter alia the corresponding N-hydroxymethylamine, e.g., morpholinomethanol. Normally, the exothermic reaction has finished within about 1 to 2 hours. The thus-produced Mannich reagent can be stored for several weeks at room temperature.

It is surprising and an advantage of the process in accordance with the invention that the use of a solvent can be dispensed with in the production of the Mannich reagent.

The aminomethylation procedure using the Mannich reagent is carried out by adding the Mannich reagent produced as described above to the δ-tocopherol or to a tocopherol mixture containing δ-tocopherol, or by performing the reverse addition, and heating the reaction mixture resulting therefrom while stirring in the temperature range between about 100° C. and about 140° C.

Preferably, about 2.5 to 10 mole equivalents of Mannich reagent (based on the amount of secondary amine or formaldehyde used for its production, depending on which amount is smaller and accordingly determinative) are used per mole equivalent of δ-tocopherol or total present non-α-tocopherols (δ-tocopherol as well as β-tocopherol and/or γ-tocopherol). The pressure under which the reaction is carried out is not critical. Thereaction can be carried out under normal pressure or under elevated pressure, for example in the latter case by carrying out the reaction in a sealed autoclave.

Thus, a further aspect of the invention is a process for the bis-aminomethylation of the unsubstituted positions on the benzene ring of δ-tocopherol, which process comprises forming a reaction mixture of a Mannich reagent and said δ-tocopherol wherein the mole ratio of said Mannich reagent to said δ-tocopherol in said reaction mixture is in a range from 2.5:1 to 10:1, said Mannich reagent being obtained by a process which comprises reacting formaldehyde or a formaldehyde-producing compound in the absence of an inert solvent with a secondary amine of the formula:

wherein $R^1$ and $R^2$ are as described above,
wherein the ratio of said formaldehyde or formaldehyde-producing compound to said secondary amine in said reaction in mole equivalents is in the range from 0.7:1 to 1.2:1, to obtain said Mannich reagent,
by which process the benzene ring of said δ-tocopherol is bis-aminomethylated.

Since it is known that vegetable oils and fats such as, for example, soya oil, rape oil, cotton seed oil, peanut oil, wheatgerm oil, corn oil, barley oil, rye oil, thistle oil and the like are valuable natural sources of tocopherols (inter alia α- and δ-tocopherol), such oils or their distillates, which have a high content of tocopherols and little undesired extraneous components, e.g., sterols, free and esterified fatty acids, waxes and glycerides, can be used as the starting material in the aminomethylation process in accordance with the invention. In particular, thistle oil and soya oil have been found to be valuable sources of tocopherols, inter alia α-tocopherol and the δ-tocopherol converted in accordance with the invention into this. It is, of course, unimportant that, inter alia, α-tocopherol itself is present in the educt, since the α-tocopherol does not prevent the conversion of δ-tocopherol into α-tocopherol and itself remains in unreacted form in the product of the process.

The course of the aminomethylation is conveniently followed by gas-chromatographic (GC) analysis of the reaction mixture, advantageously by GC analysis of silylated samples. In this way, the decreasing content of the respective 5-aminomethyl-δ-tocopherol and the correspondingly increasing content of the respective 5,7-bis(aminomethyl)-δ-tocopherol are established. Normally, the aminomethylation has finished within about 3 to 8 hours. The excess Mannich reagent may be recovered by distillation.

A further advantage of the aminomethylation process in accordance with the invention is that the distillatively separated excess Mannich reagent can, after regeneration, be used for further aminomethylations. The reuse of the Mannich reagent can be repeated several times with good results. The regeneration itself is conveniently carried out by adding water to the distillatively-separated excess Mannich reagent at room temperature and, while stirring, heating the resulting aqueous mixture to about 80° C. and subsequently adding further formaldehyde, preferably in the form of paraformaldehyde, while stirring. Then, the mixture is preferably further stirred at this temperature for about an additional 3 hours. About equimolar amounts of the three reactants are suitably used in this regeneration, with the deviation preferably not being more than about 10%.

Therefore, a further aspect of the invention is a process for the regeneration of a Mannich reagent remaining after a bis-aminomethylation reaction where said remaining Mannich reagent had been obtained by a process which comprised reacting formaldehyde or a formaldehyde-producing compound in the absence of an inert solvent with a secondary amine of the formula:

wherein $R^1$ and $R^2$ are as described above,
wherein the ratio of said formaldehyde or formaldehyde-producing compound to said secondary amine in said reaction in mole equivalents was in the range from 0.7:1 to 1.2:1, to obtain
said Mannich reagent,
said regeneration comprising:
separating said Mannich reagent from said bis-aminomethylation reaction, and reacting said separated Mannich reagent with about equimolar amounts of water and formaldehyde or a formaldehyde-forming compound to regenerate said Mannich reagent.

The regeneration reaction may be carried out at any temperature sufficient to regenerate said Mannich reagent. Preferably, the temperature is in the range from 70° C. to 90° C., especially about 80° C.

As an alternative to the use of the Mannich reagent which has been prepared essentially solvent-free, there can be used in the aminomethylation process of the invention a Mannich reagent which has been prepared from the respective diaminomethane (prepared from a secondary amine), e.g., dimorpholinomethane, and formaldehyde (preferably as paraformaldehyde) as well as water in about equimolar amounts. Preferably, these equimolar amounts do not deviate by more than about 10%. The three reactants are heated to about 70–90° C. and reacted with one another at this temperature for usually not more than about three hours, preferably about 1 to 1½ hours.

Thus, a further aspect of the invention is a process for the production of a Mannich reagent, which process comprises reacting about equimolar amounts of a compound of the formula:

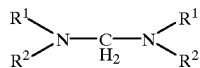

wherein $R^1$ and $R^2$ are as described above,
with formaldehyde or a formaldehyde-producing compound, and water, to produce said Mannich reagent.

In contrast to the production of the Mannich reagent from the secondary amine and formaldehyde, the present reaction is not especially exothermic. The product hardly differs in its composition and activity from the Mannich reagent of the essentially solvent-free process and from regenerated Mannich reagent. The production of the Mannich reagent in this manner can even be carried out in the presence of the δ-tocopherol or of a tocopherol mixture containing this tocopherol, so that the aminomethylation itself immediately follows the production of the Mannich reagent.

The production and use of the two "alternative" Mannich reagents form further aspects of the present invention.

The aforementioned diaminomethanes are either known or can be produced according to methods known per se, especially starting from the corresponding secondary amines.

In order finally to proceed to the desired α-tocopherol, the product of the aminomethylation in accordance with the invention, which contains a high amount of diaminomethylated δ-tocopherol and, depending on the tocopherol mixture (educt) used, monoaminomethylated β- and/or γ-tocopherol, as well as unchanged, originally-present α-tocopherol, can be reduced, e.g., catalytically hydrogenated to the desired α-tocopherol. This hydrogenation can be effected by any conventional means [see, for example, EP 159 018, U.S. Pat. No. 2,486,539 as well as U.S. Pat. No. 2,519,863].

The hydrogenation is preferably carried out using a palladium catalyst in a non-polar solvent, e.g., a dialkyl ether, especially tert.butyl methyl ether, or a hydrocarbon, e.g., n-hexane or cyclohexane. The hydrogenation requires according to experience reaction temperatures of about 150° C. to about 210° C. a hydrogen pressure of about 15 to about 50 bar as well as a reaction time of about 2 to about 10 hours. The isolation and purification of the desired α-tocopherol following hydrogenation can also be effected according to methods known per se.

The present invention embraces as a further aspect the novel bis(aminomethyl)-δ-tocopherols, i.e. the novel disubstituted [bis(aminomethylated)] δ-tocopherols manufacturable in accordance with the invention from the respective Mannich reagents and δ-tocopherol, namely of the formula:

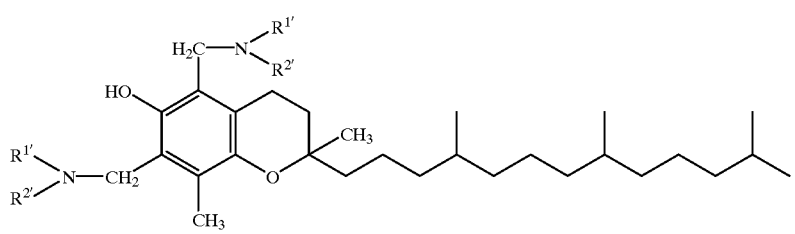

I wherein $R^{1'}$ and $R^{2'}$ are the same or different and are $C_{2-6}$-alkyl, $C_{2-6}$-hydroxyalkyl or $C_{2-6}$-alkoxyalkyl, or taken together with the nitrogen atom to which they are attached form a 5- to 8-membered heterocyclic ring, which is unsub stituted or substituted by $C_{1-6}$-alkyl, and which heterocyclic ring contains at most one additional heteroatom selected from the group consisting of oxygen and nitrogen.

In the case of the substituted cyclic amino group there come into consideration as substitutents especially lower alkyl groups (primarily $C_{1-6}$-alkyl groups). When not taken together with the nitrogen to which they are attached to form a heterocyclic ring, $R^{1'}$ and $R^{2'}$ are preferably independently ethyl, hydroxyethyl or methoxyethyl. More preferably $R^{1'}$ and $R^{2'}$ are the sane. When taken together with the nitrogen atom to which they are attached to form a heterocyclic ring, rings of 5 or 6 members are preferred. Preferred heterocyclic groups $R^{1'}R^{2'}N$ are pyrrolidino, piperidino., N-methylpiperazino and morpholino.

Formula I, in which the abbreviated form of representation usual in tocopherol chemistry (using simple lines) is used, embraces isomeric forms, especially optically active isomers, as well as mixtures thereof unless expressly mentioned to the contrary. As examples of chiral (optically active) centres there are to be mentioned the carbon atom carrying the methyl group and the 4,8,12-trimethyltridecyl group (denoted as 2 in formula I) as well as the 4- and 8-carbon atoms of the said trimethyltridecyl group (denoted as 4' and 8', respectively).

Six aforementioned specific novel compounds of formula I as well as three other novel compounds of formula I were obtained after chromatography on silica gel as colourless or light yellowish, viscous oils starting from natural d-tocopherol in each case having the 2R,4'R,8'R configuration. The $^1$H-NMR spectra obtained for these disubstituted δ-tocopherols had no signals between 5 and 9 ppm, which demonstrates the complete substitution of thebenzene nucleus. The physical data of the nine compounds are given in the following Table in which "c %" signifies concentration in weight percent:

| $R^{1'}/R^{2'}$ or heterocyclic group $R^{1'}R^{2'}N$, as appropriate | $[α]^D$ (at 20° C., c = 1%) | Content of analyzed sample (GC area %) | Extract from $^1$H-NMR spectrum (CDCl$_3$): R—CH$_2$— | Mass spectrum |
|---|---|---|---|---|
| Ethyl/Ethyl | +1.3° in C$_2$H$_5$OH | 98.7% | 3.67(s, 2H); 3.59(s, 2H). | EI-MS: 572(6, M); 499 (57, M—C$_4$H$_{11}$N); 470 (80); 428(100, 499 —C$_4$H$_9$N); 426(57, 499 —C$_4$H$_{11}$N). |
| n-Propyl/n-Propyl | +1.4°, in CHCl$_3$ | 98.6% | 3.66(s, 2H); 3.57(s, 2H). | ISP-MS: 629.7(100, M+H); 528.4(39, M —C$_6$H$_{14}$N) |
| n-Butyl/n-Butyl | +2.7°, in CHCl$_3$ | 98.0% | 3.65(s, 2H); 3.56(s, 2H). | ISP-MS: 685(100, M+H); 556(15, M —C$_8$H$_{18}$N). |
| n-Butyl/methyl | +1.2°, in CHCl$_3$ | 99.4% | 3.58(s, 2H); 3.51(s, 2H). | EI-MS: 601(7, M+H); 543 (7, M—C$_4$H$_9$); 513(100, M —C$_5$H$_{13}$N); 498(14, M —C$_5$H$_{13}$N—CH$_3$); 456(65, M —C$_5$H$_{13}$N—C$_4$H$_9$; 428 (85, 513 —C$_5$H$_{11}$N); 165 (77, —C$_{10}$H$_{13}$O$_2$). |
| Methoxyethyl/Methoxyethyl | +2.3°, in CHCl$_3$ | 99.1% | 3.78(s, 2H); 3.71(s, 2H). | EI-MS: 693(5, M+H); 560 (21, M —C$_6$H$_{14}$NO$_2$); 500 (19, M —C$_6$H$_{15}$NO$_2$ —C$_3$H$_7$O); 428(12, 560 —C$_6$H$_{14}$NO$_2$); 426(13, M -2 C$_6$H$_{15}$NO$_2$); 165(95, —C$_{10}$H$_{13}$O$_2$); 133(18, —C$_6$H$_{15}$NO$_2$); 88(100, —C$_4$H$_{10}$NO). |
| Morpholino | +2.1° in C$_2$H$_5$OH | 96.2% | 3.63(s, 2H); 3.56(s, 2H). | EI-MS: 600(10, M); 513 (100, M —C$_4$H$_9$NO); 428 (85, 513-C$_4$H$_7$NO); 426 (90, 513-C$_4$H$_9$NO). |
| Piperidino | +2.3°, in C$_2$H$_5$OH | 94.6% | 3.57(s, 2H); 3.50(s, 2H). | ISP-MS: 597(20, [M+H]$^+$); 512(100, 597 —C$_5$H$_{11}$N). |
| Pyrrolidino | +2.4°, in C$_2$H$_5$OH | 92.2% | 3.76(s, 2H); 3.71(s, 2H). | EI-MS: 568(16, M); 497 (85, M —C$_4$H$_9$N); 428(100, 497 —C$_4$H$_7$N); 427(60, 497 —C$_4$H$_8$N). |
| N-Methylpiperazino | +2.8°, in C$_2$H$_5$OH | 99.3% | 3.63(s, 2H); 3.56(s, 2H). | EI-MS: 626(2, M); 526 (34, M —C$_5$H$_{12}$N$_2$); 428 (12, 526 —C$_5$H$_{10}$N$_2$); 426 (11, 526 —C$_5$H$_{12}$N$_2$); 99 (100, —C$_5$H$_{11}$N$_2^+$). |

5,7-Bis(morpholinomethyl)-δ-tocopherol and 5,7-bis(N-methylpiperazinomethyl)-δ-tocopherol are especially preferred bis(aminomethyl)-δ-tocopherols of formula I.

A further advantage is present in the aminomethylation process which is used for the production of the disubstituted δ-tocopherols: where the educt (δ-tocopherol) is a pure isomer, e.g., is in the 2R,4'R,8'R configuration, the stereochemical purity is retained in the 5,7-disubstituted (aminomethylated) product.

The present invention is illustrated by the following Examples:

EXAMPLE 1
Production of a "Mannich Reagent"

30.0 g (1.0 mol) of paraformaldehyde are added portionwise at about 70° C. and while stirring to 87.0 ml (87.0 g, 1.0 mol) of morpholine in such a manner that the temperature rises to a maximum of 80° C., the addition taking a total of about 30 minutes. After about 1½ hours the exothermic reaction has finished with the formation of a colourless liquid. According to $^1$H-NMR and $^{13}$C-NMR analysis a multicomponent mixture is present, about half of which consists of dimorpholinomethane. This mixture (the "Mannich reagent") can be stored at room temperature for at least several weeks.

EXAMPLE 2
Production of a "Mannich Reagent"

30.0 g (1.0 mol) of paraformaldehyde are added portionwise to 1.0 mol of secondary amine [either diethylamine, di(n-propyl)amine, di(n-butyl)amine, methylbutylamine, di(methoxyethyl)amine, morpholine, 1-methyl-piperazine, piperidine or pyrrolidine] at 70–80° C. (at 50° C. in the case of diethylamine) and while stirring in such a manner that the temperature rises to a maximum of 90° C. After completion of the addition, which takes about 15 to 45 minutes depending on the secondary amine used, the mixture is stirred at 70–80° C. for a further 2 hours and cooled to room temperature. The residual colourless to slightly brownish liquids ("Mannich reagents"), which in some cases consist of two phases, can be used directly for the aminomethylation of non-α-tocopherols or tocopherol mixtures.

EXAMPLE 3
Production of a "Mannich Reagent" (Alternative)

18.0 g (1.0 mol) of water are added dropwise while stirring within 10 minutes to 102.2 g (1.0 mol) of bis(almethylamino)-methane, with the mixture warming slightly from 23° C. to 30° C. Then, the resulting two-phase mixture is heated to 80° C., 30.0 g (1.0 mol) of paraformaldehyde are introduced portionwise within about 10 minutes, the mixture is stirred at 80° C. for a further 2 hours and left to cool to room temperature. The resulting colourless, clear solution ("Mannich reagent") can be used directly for the aminomethylation of non-α-tocopherols or tocopherol mixtures.

EXAMPLE 4
Aminomethylation with a Mannich Reagent and Subsequent Catalytic Hydrogenation 46.8 g (0.4 mol) of Mannich reagent (prepared according to Example 1) are added while stirring to a tocopherol mixture consisting mainly of δ-tocopherol (42 g, about 0.1 mol: 85.5% δ-, 4.6% γ- as well as 0.5% α-tocopherol). The homogeneous mixture is heated at 130° C. for 9 hours, during which resulting water is evaporated off. After this reaction time the aminomethylation product consists, according to gas-chromatographical (GC) analysis, of 5,7-bis(morpholinomethyl)-δ-tocopherol (92.5%), 5-morpholino-methyl-γ-tocopherol (4.2%), 5-morpholinomethyl-δ-tocopherol (0.6%) as well as α-tocopherol (0.6%).

The above aminomethylation product is hydrogenated at 180° C. and 20 bar for 20 hours using 10% palladium on carbon as the catalyst in tert.butyl methyl ether (about 10% solution). In this manner there is obtained an almost quantitative yield of a-tocopherol (GC analysis: 97.0% a-, 1.9% b- as well as 0.9% g- tocopherol).

EXAMPLE 5
Aminomethylation with a Mannich Reagent 440 g (1.0 mol) of a tocopherol mixture consisting of 4.6% α-, 1.0% β-, 58.8% γ- as well as 30.2% δ-tocopherol are dissolved while stirring in 705 g of a Mannich reagent prepared according to Example 1, with the temperature of the reaction mixture rising to about 35° C. (due no doubt to the beginning of amino-methylation). After about one hour the mixture is heated to an internal temperature of 110° C. (heating bath temperature about 140° C.), during which resulting water is evaporated off. The reaction temperature increases to 130° C. within a further 1½ hours, and after a further 4 hours at this temperature the reaction has finished. The aminomethylation product (1005 g) consists according to GC analysis of α-tocopherol (4.0%), 7-morpholinomethyl-β-tocopherol (2.0%), 5-morpholinomethyl-γ-tocopherol (59.8%), 5,7-bis(morpholinomethyl)-δ-tocopherol (32.6%) as well as 5-moiphol-inomethyl-δ-tocopherol (0.4%).

Subsequently, the aminomethylation product is freed in a falling film evaporator from excess Mannich reagent (mainly dimorpholinomethane).

EXAMPLE 6
Aminomethylation with a Mannich Reagent and Subsequent Catalytic Hydrogenation 218.35 g (0.5 mol) of a tocopherol mixture consisting of 4.6% α-, 1.0% β-, 58.8% γ- as well as 30.2% δ-tocopherol are dissolved while stirring in 300 g (2.56 mol) of a Mannich reagent prepared according to Example 1. A reaction temperature of 105° C. is reached after about 30 minutes with a heating bath temperature of 120° C., with resulting water being evaporated off. The reaction temperature rises to 117° C. within a further 4 hours. The reaction mixture is stirred at this temperature for a further 4¾ hours and subsequently left to cool to room temperature. The aminomethylation product (456.4 g) consists according to GC analysis of α-tocopherol (3.55%), 7-morpholinomethyl-β-tocopherol (1.7%), 5-morpholinomethyl-γ-tocopherol (60,1%), 5,7-bis(morpholinomethyl)-δ-tocopherol (32.86%) as well as 5-morpholinomethyl-δ-tocopherol (0.2%).

Subsequently, the aminomethylation product is freed in a falling film evaporator from excess Mannich reagent (mainly dimorpholinomethane).

The above aminomethylation product, freed from excess Mannich reagent, is hydrogenated at 180° C. and 30 bar for 5 hours using 10% palladium on carbon as the catalyst in tert.butyl methyl ether (about 10% solution). In this manner there is obtained an almost quantitative yield of a-tocopherol (GC analysis: 98.0% α-, 0.8% β- as well as 1.2% γ-tocopherol).

EXAMPLE 7

Aminomethylation with a Mannich Reagent in an Autoclave 172.44 g (0.4 mol) of a tocopherol mixture consisting of 0.4% α-, 64.9% γ- as well as 30.3% δ-tocopherol are dissolved while stirring in 247.5 g of a Mannich reagent produced according to Example 1. The reaction mixture is charged into a 2 l laboratory autoclave (Buichi BEP 280 Type IV, steel). The autoclave is sealed and the reaction mixture is heated to 118° C. (internal temperature) while stirring. The complete course of the reaction is followed by gas-chromatographical determination of the decreasing content of 5-morpholinomethyl-δ-tocopherol: reaction time 2 hours: 1.2%; reaction time 3 hours: 0.3%; reaction time 4 hours: <0.1%. After a total of 4½ hours (pressure increase to 4.1 bar) the reaction mixture is cooled to 30° C. The thus-obtained aminomethylation product consists according to GC analysis of α-tocopherol (0.35%), 5-morpholinomethyl-γ-tocopherol (66.3%) as well as 5,7-bis(morpholinomethyl)-δ-tocopherol (33.4%).

EXAMPLE 8

Production of a Mannich Reagent and Subsequent Aminomethylation 6.7 ml (6 g, 60 mmol) of 1-methylpiperazine are introduced at room temperature under argon into a 50 ml three-necked flask equipped with an internal thermometer and magnetic stirrer and heated to 60° C. 1.8 g (60 mmol) of paraformaldehyde are added portionwise to the 1-methyl-piperazine within 10 minutes. Subsequently, the mixture is stirred at 60° C. for a further. 30 minutes.

Subsequently, 4.2 g (about 10 mmol) of δ-tocopherol are added to the thus-obtained homogeneous solution (the Mannich reagent) and the reaction mixture is heated to 120° C. within 30 minutes and at this temperature for about a further 2½ hours. The course of the reaction is followed by GC analysis of silylated samples in order to determine the percentage content of mono- and disubstituted product [mainly 5-(N-methyl-piperazinomethyl)-δ-tocopherol and 5,7-bis(N-methyl-piperazinomethyl)-δ-tocopherol, respectively], with the following results:

| Reaction time (hours from initial addition) | Content of Monosubst. product | Disubst. product |
|---|---|---|
| 0.25 | 5.9% | 84.6% |
| 1.5 | 1.3% | 92.8% |
| 3.0 | 0% | 93.6% |

EXAMPLE 9

Aminomethylation of D-Tocopherol with a Mannich Reagent in anAutoclave and Subsequent Catalytic Hydrogenation According to the details given in the following Table, 0.3 or 0.5 mol (6 or 10 mol equivalents based on total tocopherols) of Mannich reagent (produced according to Example 1, 2, 3, 8 or 11) as well as in two instances N,N,N',N'-tetramethylethylenediamine (100 wt. % based on Mannich reagent used) as a solvent aid (solubilizer) is added to 22.32 g of d-d-tocopherol [from the firm Sigma; about 90%, content of: d-tocopherol 86.6%, 48.0 mmol; g-tocopherol 3.7%, 1.96 mmol; a-tocopherol 0.1%, 0.04 mmol; total tocopherols 90.4%, 50.0 mmol; determined by GC of the acetates, internal standard squalane; stereochemical purity: 94.95% R,R,R-δ- and 4.87% R,R,R-γ-homologues, total 99.82% R,R,R-tocopherols; determined by HPLC of the methyl ether derivative on Chiracel OD, a commercially available chromatography column from the firm Daicel] in a 185 ml steel autoclave having a mechanical stirrer, and the mixture is stirred in the sealed autoclave at 600 rpm for 24 hours at 120° C. or 140° C. Brown oils are obtained for the most part. In some cases a small lower phase (maximum 13 wt. %) separates; this is removed and discarded. For analysis, a small sample of the crude product [N,O-bis(trimethylsilyl)-trifluoroacetamide/pyridine] is silylated, and the results given in the following Table are obtained.

| Amine component $NR^1R^2$ | Reaction temperature (° C.) | Mol equivalent of Mannich reagent | Added solubilizer | Ratio (GC area % after silylation)[1] mono-substituted product | di-substituted product |
|---|---|---|---|---|---|
| $R^1 = R^2 =$ Methyl | 140 | 10 | — | 0.9 | 94.4 |
| $R^1 = R^2 =$ Ethyl | 140 | 10 | N,N,N',N'-Tetra-methyl-ethylenedi-amine | 3.7 | 92.7 |
| $R^1 = R^2 =$ n-Propyl | 140 | 6 | N,N,N',N'-Tetra-methyl-ethylenedi-amine | 1.1 | 95.5 |
| $R^1 = R^2 =$ n-Butyl | 140 | 10 | — | 2.5 | 93.5 |
| $R^1 =$ Methyl $R^2 =$ n-Butyl | 120 | 6 | — | 2.0 | 94.6 |
| $R^1 = R^2 =$ Methoxy-ethyl | 140 | 10 | — | 2.5 | 93.8 |
| Morpholino | 120 | 6 | — | 0 | 94.4 |
| N-Methyl-piperazino | 120 | 6 | — | 0 | 95.6 |

-continued

| Amine component $NR^1R^2$ | Reaction temperature (° C.) | Mol equivalent of Mannich reagent | Added solubilizer | Ratio (GC area % after silylation)[1] | |
|---|---|---|---|---|---|
| | | | | mono-substituted product | di-substituted product |
| Pyrrolidino | 120 | 6 | — | 3.3 | 92.4 |
| Piperidino | 140 | 10 | — | 1.2 | 95.3 |

[1]monosubstituted product = 5-dialkylaminomethyl-d-tocopherol, disubstituted product = 5,7-bis(dialkylaminomethyl)-d-tocopherol; additionally 3.4–4.4% of 5-dialkylaminomethyl-g-tocopherol and traces (about 0.1%) of a-tocopherol.

The thus-obtained crude aminomethylation products are hydrogenated in batches of 1–10 mmol with 10% palladium on carbon (Degussa E 101 N/D, 1.0 g for 10 mmol) in tert.butyl methyl ether as the solvent for 20 hours and while stirring at 180° C. under 20 bar hydrogen pressure. After completion of the reaction the catalyst is filtered off over Speedex (filter aid) and rinsed with tert.butyl methyl ether, and the solvent is distilled off under reduced pressure, with the yields of tocopherols being determined quantitatively by GC (after acetylation with acetic anhydride/pyridine/dimethylaminopyridine). Some details are given in the following Table.

| Crude product used: aminomethylation product; amine component $NR^1R^2$ | Concentration of the hydrogenation solution (g crude product used per 100 ml) | Chemical yields of tocopherols (GC of the acetates, internal standard squalane) in % (based on total tocopherol used) | | |
|---|---|---|---|---|
| | | alpha-Tocopherol | beta-Tocopherol | gamma-Tocopherol |
| $R^1 = R^2$ = n-Propyl | 6 | 94.4 | 1.9 | 1.5 |
| $R^1 = R^2$ = n-Butyl | 25 | 90.0 | 2.6 | 1.0 |
| $R^1$ = Methyl, $R^1$ = n-Butyl | 13 | 96.5 | 2.9 | 0.0 |
| $R^1 = R^2$ = Methoxyethyl | 24 | 81.1 | 2.3 | 0.9 |
| Morpholino | 13 | 90.3 | 1.2 | 0.6 |
| N-Methyl-piperazino | 16 | 87.5 | 4.3 | 1.6 |
| Pyrrolidino | 2 | 82.2 | 4.9 | 2.3 |
| Piperidino | 2 | 83.4 | 1.4 | 0.9 |

EXAMPLE 10
Aminomethylation of a Tocopherol Mixture with Dimorpholinomethane, Formaldehyde and Water in an Autoclave 11.5 g (total 0.033 mol) of a tocopherol mixture (3.6% α-, 1.3% β-, 62.8% γ-, 28.0% δ-tocopherol), 37.2 g (0.2 mol) of dimorpholinomethane, 6.0 g (0.2 mol) of paraformaldehyde and 3.6 g (0.2 mol) of water are introduced in succession at room temperature into a 185 ml steel autoclave having a mechanical stirrer. The autoclave is sealed and the reaction mixture is stirred at 130° C. for 15 hours. After cooling a sample of the reaction mixture is silylated and the content of tocopherols and aminomethylated tocopherols is determined by gas chromatography: α-tocopherol (3.0%), 7-morpholinomethyl-β-tocopherol (2.1%), 5-morpholinomethyl-γ-tocopherol (64.6%) as well as 5,7-bis(morpholinomethyl)-δ-tocopherol (29.2%).

EXAMPLE 11
Regeneration of a Manich Reagent

The excess of the Mannich reagent used for the aminomethylation can be recovered by distillation after the aminomethylation has finished. Such a distillate [205.8 g of water-clear liquid; consisting according to $^1$H-MMR of an about 6:1 mixture of dimorpholinomethane (about 1.0 mol) and N-hydroxymethyl-morpholine] is treated with 18 g (1.0 mol) of water at room temperature while stirring. The resulting aqueous mixture is heated in an oil bath to 80° C., and 30 g (1.0 mol) of paraformaldehyde are added portionwise within one hour. The mixture is stirred for a further 3 hours, resulting in a colourless, almost clear solution. The $^1$H-NMR spectrum of this thus-regenerated Mannich reagent corresponds almost exactly to the $^1$H-NMR spectrum of a freshly produced Mannich reagent (such as, for example, produced according to Example 1).

What is claimed is:

1. A process for the production of a Mannich reagent, which process comprises reacting about equimolar amounts of a compound of the formula:

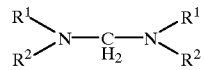

wherein $R^1$ and $R^2$ are the same or different and are $C_{1-6}$-alkyl, $C_{2-6}$-hydroxyalkyl or $C_{2-6}$-alkoxyalkyl, or taken together with the nitrogen atom to which they are attached form a 5- to 8-membered heterocyclic ring, which is unsubstituted or substituted by $C_{1-6}$-alkyl, and which heterocyclic ring contains at most one additional heteroatom selected from the group consisting of oxygen and nitrogen,
with formaldehyde or a formaldehyde-producing compound, and water, to produce said Mannich reagent.

2. The process of claim 1 wherein $R^1$ and $R^2$ are independently $C_{1-6}$-alkyl, $C_{2-6}$-hydroxyalkyl or $C_{2-6}$-alkoxyalkyl.

3. The process of claim 2 wherein $R^1$ and $R^2$ are the same and are $C_{1-6}$-alkyl, $C_{2-6}$-hydroxyalkyl or $C_{2-6}$-alkoxyalkyl.

4. The process of claim 3 wherein $R^1$ and $R^2$ are methyl.

5. The process of claim 3 wherein $R^1$ and $R^2$ are ethyl.

6. The process of claim 3 wherein $R^1$ and $R^2$ are hydroxyethyl.

7. The process of claim 3 wherein $R^1$ and $R^2$ are methoxyethyl.

8. The process of claim 1 wherein $R^1$ and $R^2$ taken together with the nitrogen atom to which they are attached form a heterocyclic ring and said heterocyclic ring contains as its only heteroatom the nitrogen to which $R^1$ and $R^2$ are attached.

9. The process of claim 8 wherein the heterocyclic ring is pyrrolidine.

10. The process of claim 8 wherein the heterocyclic ring is piperidine.

11. The process of claim 1 wherein $R^1$ and $R^2$ taken together with be nitrogen atom to which they are attached form a heterocyclic ring which contains an additional heteroatom selected from the group consisting of nitrogen and oxygen.

12. The process of claim 11 wherein the additional heteroatom is nitrogen.

13. The process of claim 12 wherein the heterocyclic ring is 1-methyl-piperazine.

14. The process of claim 11 wherein the additional heteroatom is oxygen.

15. The process of claim 14 wherein the heterocyclic ring is morpholine.

* * * * *

UNITED STATES PATENT AND TRADEMARK OFFICE
CERTIFICATE OF CORRECTION

Page 1 of 1

PATENT NO. : 6,252,071 B1
DATED : June 26, 2001
INVENTOR(S) : Robert Karl Müller and Heinz Schneider It is certified that error appears in the above-identified patent and that said Letters Patent is hereby corrected as shown below:

<u>Column 15,</u>
Line 6, please change "be" to -- the --.

Signed and Sealed this

Sixteenth Day of April, 2002

Attest:

JAMES E. ROGAN
*Director of the United States Patent and Trademark Office*

*Attesting Officer*